(12) United States Patent
Madsen et al.

(10) Patent No.: US 6,190,915 B1
(45) Date of Patent: Feb. 20, 2001

(54) ULTRASOUND PHANTOMS

(75) Inventors: Ernest L. Madsen; Gary R. Frank, both of Madison, WI (US)

(73) Assignee: Wisconsin Alumni Research Foundation, Madison, WI (US)

(*) Notice: Under 35 U.S.C. 154(b), the term of this patent shall be extended for 0 days.

(21) Appl. No.: 09/340,219

(22) Filed: Jun. 25, 1999

(51) Int. Cl.[7] ................................................. G01N 31/00
(52) U.S. Cl. ........................ 436/8; 422/102; 73/1.86; 73/866.4; 73/865.6; 600/437; 600/442
(58) Field of Search ................... 436/8; 73/1.86, 73/866.4, 865.6; 422/99, 102; 600/437, 442

(56) References Cited

U.S. PATENT DOCUMENTS

| | | | |
|---|---|---|---|
| 4,277,367 | 7/1981 | Madsen et al. ........................... 436/8 |
| 4,286,455 | * 9/1981 | Ophir et al. ........................... 73/1.83 |
| 4,453,408 | * 6/1984 | Clayman ............................... 73/1.86 |
| 4,843,866 | 7/1989 | Madsen et al. ........................ 73/1.86 |
| 4,974,461 | * 12/1990 | Smith et al. .......................... 73/865.6 |
| 5,052,934 | * 10/1991 | Carey et al. ........................... 434/268 |
| 5,312,755 | * 5/1994 | Madsen et al. ........................... 436/8 |
| 5,625,137 | 4/1997 | Madsen et al. ........................ 73/1.84 |
| 5,670,719 | * 9/1997 | Madsen et al. .......................... 73/619 |
| 5,902,748 | * 5/1999 | Madsen et al. ........................... 436/8 |

* cited by examiner

*Primary Examiner*—Maureen M. Wallenhorst
(74) *Attorney, Agent, or Firm*—Foley & Lardner

(57) ABSTRACT

An improved ultrasound phantom includes a container having a window covered by an ultrasound transmitting window cover that seals and protects a water based tissue mimicking material within the container. The window cover includes a multi-layer film formed of at least a layer of metal adhered to a layer of plastic. The metal layer is essentially impervious to moisture and air molecules, preventing both desiccation of the water based material within the phantom and oxidation or contamination of the tissue mimicking material. Multiple windows may be formed in the container which are closed with the multi-layer film cover, and the container may be formed entirely or partially as a flexible sack of multi-layer film.

35 Claims, 4 Drawing Sheets

Amplitude transmission coefficients for 100 micron thick plastic-coated aluminum film (○) and 50 micron thick Saran (■).

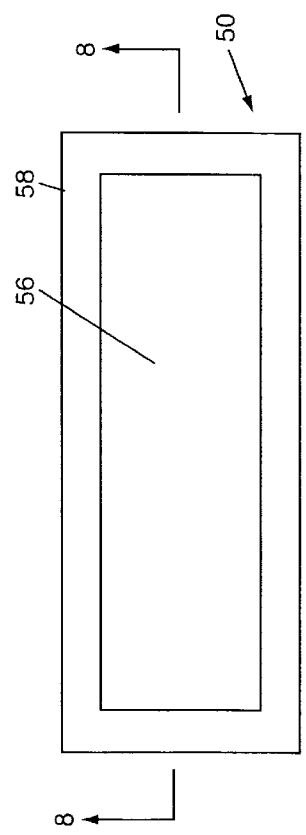
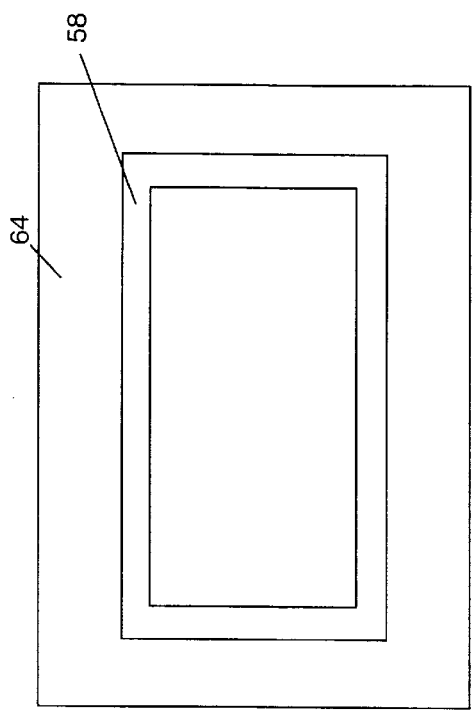
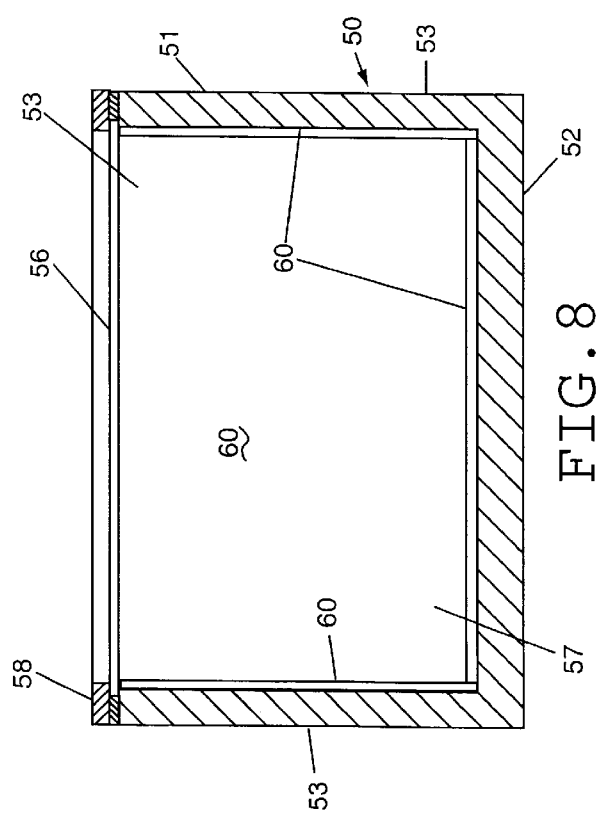
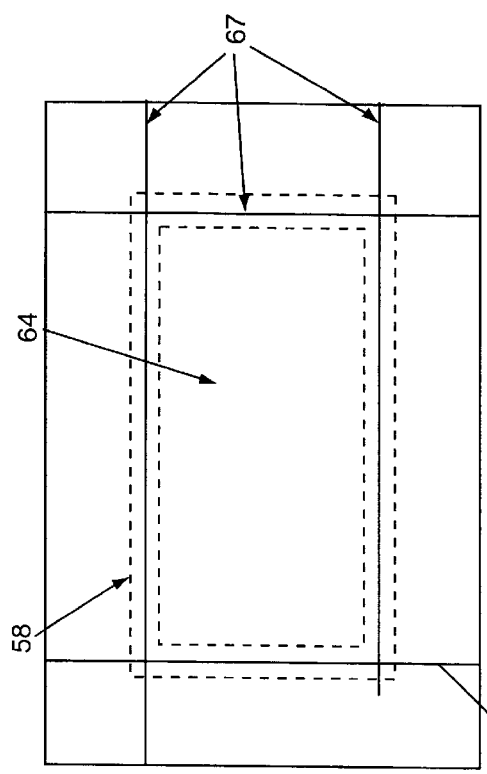

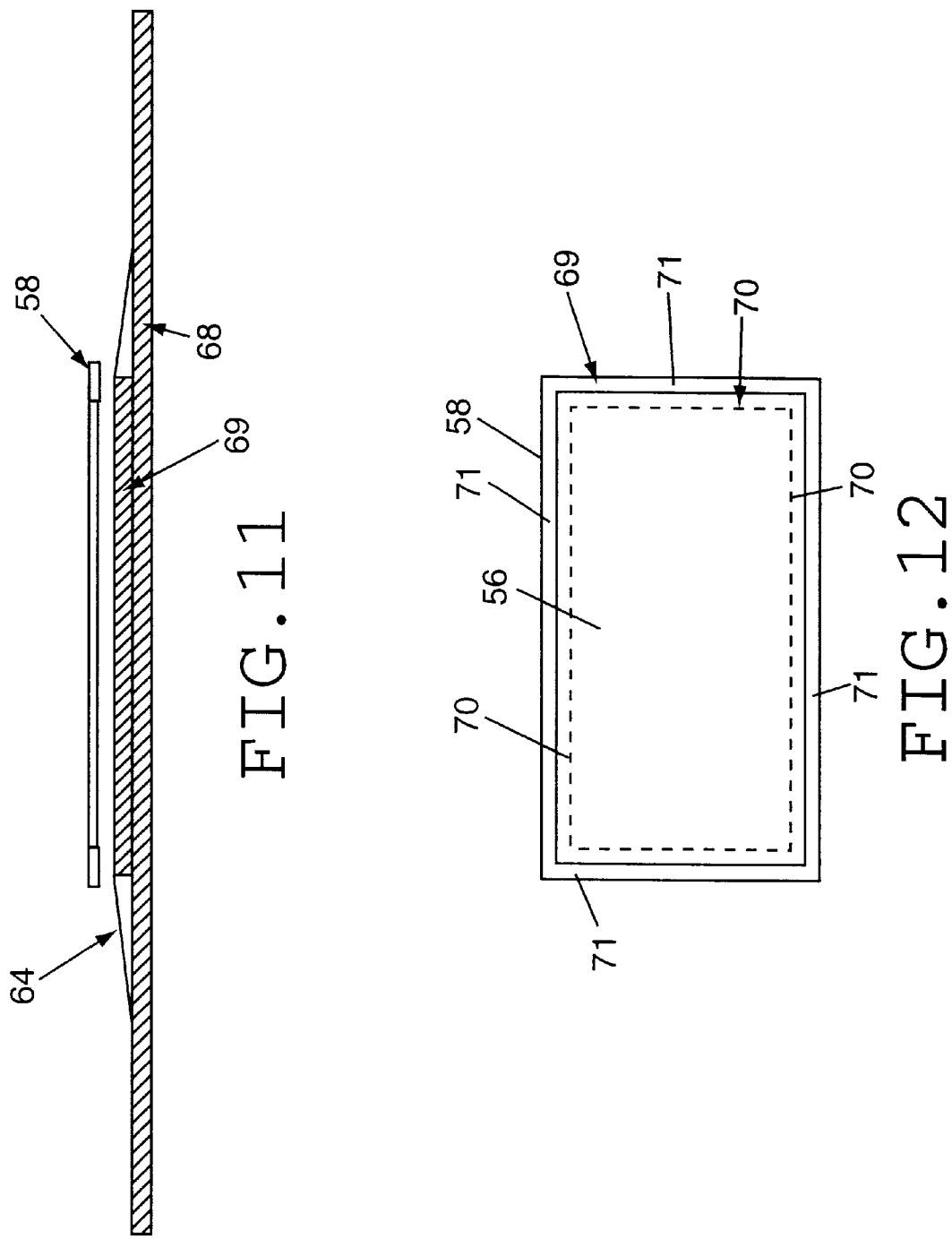

ULTRASOUND PHANTOMS

This invention was made with United States government support awarded by the following agency: NIH Grant No. GM54377. The United States government has certain rights in this invention.

FIELD OF THE INVENTION

This invention pertains generally to the field of ultrasound phantoms for use with ultrasound scanners.

BACKGROUND OF THE INVENTION

Materials which closely mimic the ultrasonic propagation characteristics of human tissue are employed in imaging phantoms and other test objects for use with ultrasound scanners. These phantoms may be used to carry out performance checks on ultrasound scanners. Phantoms may also be used for training or testing student technologists in the operation of ultrasound scanners or the interpretation of ultrasound images produced by such scanners.

A phantom containing tissue mimicking material is disclosed in U.S. Pat. No. 4,277,367, to Madsen, et al., entitled Phantom Material and Methods, in which both the speed of sound and the ultrasonic attenuation properties could be simultaneously controlled in a mimicking material based on water based gels, such as those derived from animal hides. In one embodiment, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue mimicking material.

Tissue mimicking material is typically used to form the body of an ultrasound scanner phantom. This is accomplished by enclosing the material in a container which is closed by an ultrasound transmitting window cover. The tissue mimicking material is admitted to the container in such a way as to exclude air bubbles from forming in the container. In addition to the tissue mimicking material itself, scattering particles, spaced sufficiently close to each other that an ultrasound scanner is incapable of resolving individual scattering particles, and testing spheres or other targets, may be located within the phantom container, suspended in the tissue mimicking material body. Such an ultrasound phantom is useful in evaluating the ability of ultrasound medical diagnostic scanners to resolve target objects of selected sizes located throughout the tissue mimicking material. The objective is for the ultrasound scanner to resolve the testing spheres or other targets from the background material and scattering particles. This type of ultrasound phantom is described in U.S. Pat. No. 4,843,866, to Madsen, et al., entitled Ultrasound Phantom.

U.S. Pat. No. 5,625,137 to Madsen, et al. discloses a tissue mimicking material for phantoms with very low acoustic backscatter coefficient that may be in liquid or solid form. A component in both the liquid and solid forms is a filtered aqueous mixture of large organic water soluble molecules and an emulsion of fatty acid esters, which may be based on a combination of condensed milk and water. Hydroxy compounds, such as n-propanol, can be used to control the ultrasonic speed of propagation through the material and a preservative from bacterial invasion can also be included. The use of scattering particles allows a very broad range of relative backscatter levels to be achieved.

The tissue mimicking material in ultrasound phantoms is typically water based to best simulate human tissue. The tissue mimicking material may be either in liquid form or in a solid gel form. As discussed in greater detail in the foregoing patents, the tissue mimicking material is typically held within a container having a bottom and upright walls which may be molded as a unit or formed of flat pieces of plastic or other materials glued or otherwise joined together. Such rigid walls would not permit the transmission of ultrasound from a transducer through the walls to the tissue mimicking material within the container. The container cannot be left open to expose the tissue mimicking material since to do so would allow evaporation of the water within the material as well as potential oxidation or contamination of the material. Thus, the open tops of the phantom containers are typically sealed with a thin sheet of plastic such as polyurethane or saran (e.g., Saran Wrap®) to protect the tissue mimicking material from physical contact with the transducer and to minimize moisture loss from the material. The thin sheets of plastic are flexible and thin enough to transmit ultrasound therethrough to the tissue mimicking material without substantial attenuation or degradation of the signal, but are not entirely impervious to water vapor or air gas molecules such as oxygen. Consequently, gel based phantoms have commonly been made using a layer of oil based gel covering the tissue mimicking material gel, with the flexible plastic cover in contact with the oil based gel. The oil based gel reduces water loss through the window but does not entirely eliminate it, and the use of an oil gel adds an additional layer of material through which the ultrasound must be transmitted from the transducer to the tissue mimicking material and back again. The oil based gels can detach from the plastic cover and walls of the phantom, allowing rapid desiccation of the phantom contents. In addition, even with the oil based gel in proper position, significant desiccation can occur.

SUMMARY OF THE INVENTION

In accordance with the invention, an improved ultrasound phantom has a container with a bottom and walls, with margins of the walls defining a window which is covered by an ultrasound transmitting window cover sealed to the margins of the window to close the window. The window cover contacts and protects a phantom body contained within the container which comprises a water based liquid or solid gel tissue mimicking material. The window cover comprises a multi-layer film formed of at least a layer of metal adhered to a layer of plastic and may comprise a layer of metal foil between layers of plastic. The metal layer, e.g., aluminum foil, is essentially impervious to moisture and air molecules, preventing both desiccation of the water based material within the phantom and oxidation or contamination of the tissue mimicking materials. Even though the multi-layer film includes a layer of metal, the ultrasound energy from the transducer is readily transmitted through the multi-layer cover without substantial attenuation and without excessive echoes from the multi-layer film that might otherwise degrade the ability of the ultrasound transducer to test the tissue mimicking material within the phantom container.

The ultrasound phantom of the invention may further incorporate a window opening in a side wall of the phantom to define a side scanning window, and include a side window cover sealed to the side wall to cover the side scanning opening, the side window cover again comprising a multi-layer film formed of a layer of metal on a layer of plastic and may comprise metal foil between layers of plastic. The phantom container may be formed closed on all sides, with the side wall opening forming the margins which define the window in the container. Alternatively, the container may be formed with top margins which define a top window for the container which is closed by a multi-layer film in accordance with the invention, and with a side window opening in a side wall which is closed by the multi-layer film in accordance with the invention, allowing access to the tissue mimicking material within the phantom by an ultrasound transducer at various, e.g., orthogonally oriented, positions.

In a further embodiment of the invention, the entire container may be formed of the multi-layer film in accordance with the invention, preferably by utilizing heat sealable thermoplastic for the layers of plastic, which are sealed together to define a flexible sack which encloses the tissue mimicking material. Despite the fact that the entire phantom is then contained within a flexible container, the very low rate of water vapor or gas transmission through the walls of the flexible container provides long-term stability for the tissue mimicking material within the container. The flexible container itself may be mounted within a bath (preferably a water bath) to enable coupling of ultrasound through a submerged hydrophone to the sack containing liquid tissue mimicking material. Further, the sack may be secured to an opening in a solid wall of the enclosure for the bath to provide a window to which an ultrasonic transducer may be applied.

A preferred material of the invention comprises a multi-layer film having an aluminum foil layer, 10 microns or less in thickness and preferably about 9 microns thick, between layers of plastic and preferably with an additional layer of polyester to form a multi-layer film about 100 microns thick.

Further objects, features and advantages of the invention will be apparent from the following detailed description when taken in conjunction with the accompanying drawings.

BRIEF DESCRIPTION OF THE DRAWINGS

In the drawings:

FIG. 7 is a top view of another ultrasound phantom in accordance with the invention.

FIG. 8 is a cross-sectional view of the phantom of FIG. 7 taken generally along the lines 8—8 of FIG. 7.

FIG. 9 is a plan view illustrating the gluing of a window frame to multi-layer film.

FIG. 10 is a plan view of the frame and multi-layer film at a further step in the assembly process.

FIG. 11 is a side view of the frame and multi-layer film during the assembly process using a fixture to facilitate attachment of the multi-layer film to the frame.

FIG. 12 is a plan view of the completed frame with the multi-layer film adhered thereto.

DETAILED DESCRIPTION OF THE INVENTION

Figure 1:
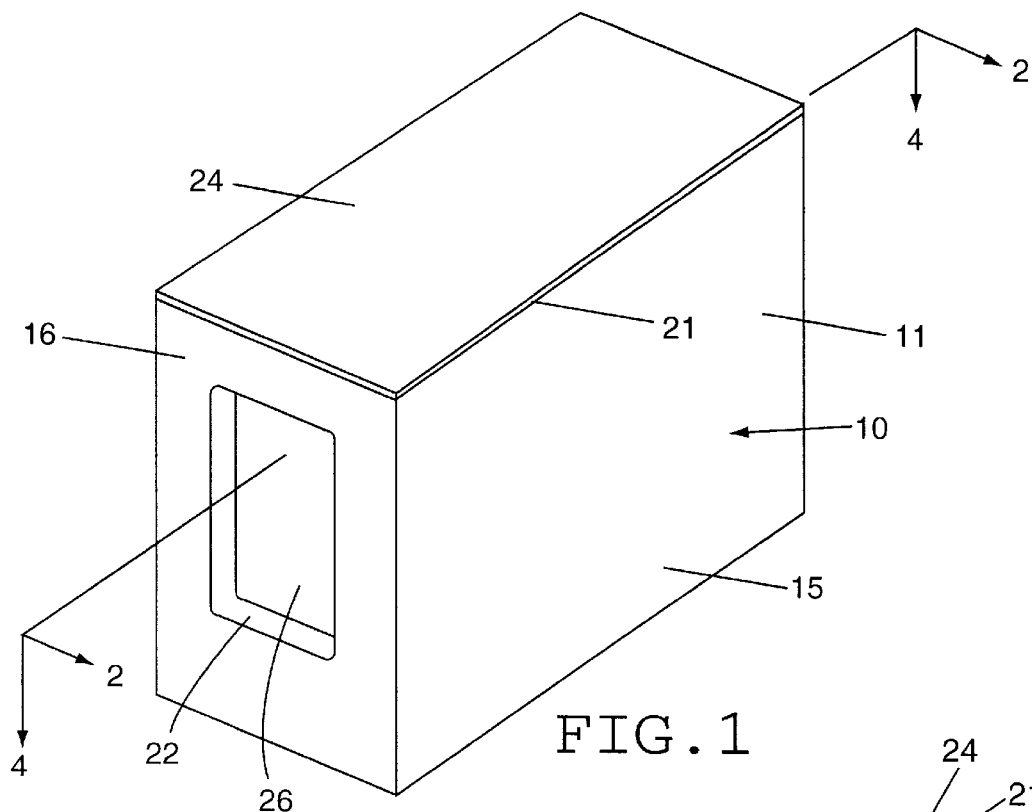
FIG. 1 is a perspective view of an ultrasound phantom in accordance with the invention.
Figure 2:
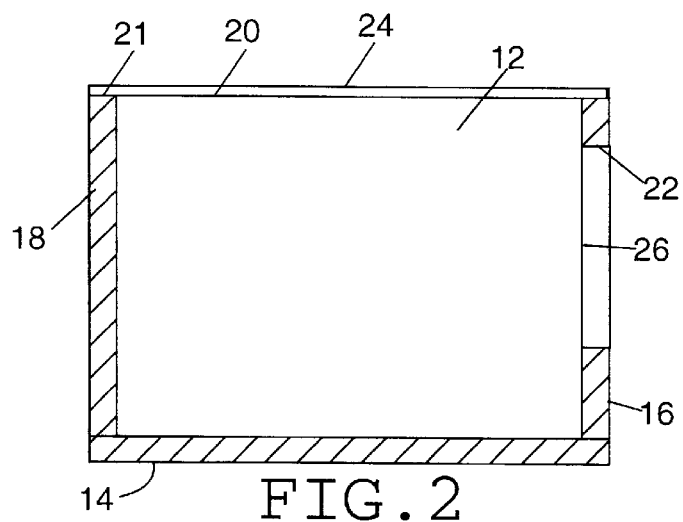
FIG. 2 is a cross-sectional view of the phantom of FIG. 1 taken generally along the lines 2—2 of FIG. 1.
Figure 3:
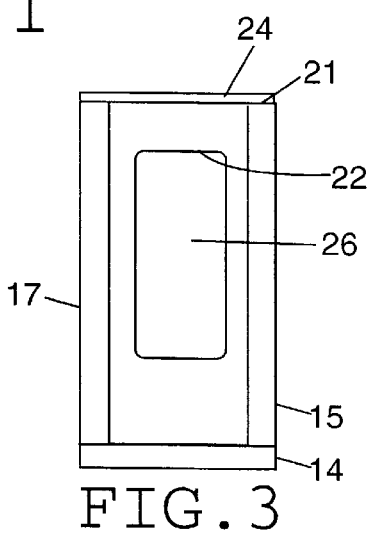
FIG. 3 is an end view of the phantom of FIG. 1.
Figure 4:
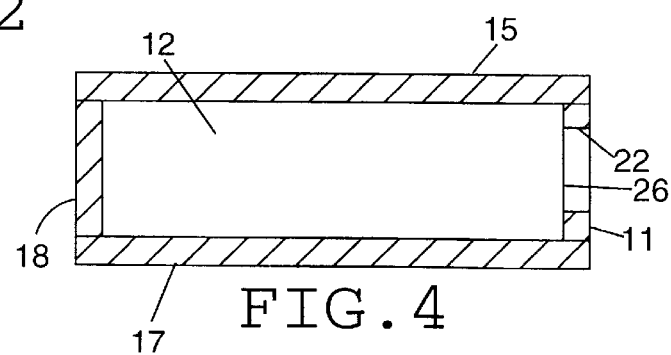
FIG. 4 is a cross-sectional view taken generally along the lines 4—4 of FIG. 1.

With reference to the drawings, a perspective view of an ultrasound phantom for use with ultrasound scanners in accordance with the invention is shown generally at 10 in FIG. 1 and in various side and cross-sectional views in FIGS. 2–4. The ultrasound phantom 10 has a rigid container 11 for holding tissue mimicking material 12, comprised of a bottom wall 14 and side walls 15, 16, 17, and 18. The physical construction of the container 11 is not crucial, and any suitable materials that will hold the tissue mimicking material 12 within the container without substantial transmission of water vapor or air molecules therethrough may be utilized, such as acrylic plastic or ABS plastic. The container may be formed by adhering together plates of plastic, etc., or by one piece molding or any other convenient manufacturing process. The container 11 may also be formed in other configurations than the rectangular configuration illustrated in the figures, e.g., cylindrical, polygonal, etc.

For purposes of illustration, the container 11 of the phantom 10 includes a top window opening 20 defined by top margins 21 of the side walls 15–18, and a side window opening 22 formed in one of the side walls (side wall 16 for illustration). The top opening 20 is covered by a top window cover 24 which is sealed to the top window margins 21, e.g., with an epoxy glue. Similarly, the side scanning window opening 22 is covered with a side scanning window cover 26 which is sealed to the margins of the wall 16 around the opening 22, e.g., by being secured with epoxy adhesive to the inner wall of the side opening 16. The side window cover 26 could be secured to the exterior wall of the wall 16, or to the interior margins of the opening 22, or in any other desired manner.

The interior of the container 11 is filled with a water based tissue mimicking material 12 which may be either in liquid or gel form. Various types of tissue mimicking materials may be utilized, as disclosed, for example, in the aforementioned U.S. Pat. Nos. 4,277,367, 4,843,866, and 5,625,137, the disclosures of which are incorporated herein by reference. The entire interior of the container 11, as sealed by the top window cover 24 and the side window cover 26, is filled with the tissue mimicking material 12 to form a tissue mimicking body which entirely occupies the space within the container and which is in direct contact with the top scanning window cover 24 and the side scanning window cover 26. The filling of the container may be carried out as set forth in the aforesaid patents, e.g., as described in U.S. Pat. No. 5,625,137, by utilizing an additional filling opening (not shown) by which the tissue mimicking material in liquid form (e.g., prior to gelling for gel based tissue mimicking material) is introduced into the interior of the container. Any other method of filling the container may also be utilized.

Prior ultrasound phantoms utilized thin sheets of plastic to cover a scanning window, e.g., films of polyurethane or saran plastics, which permitted acceptable transmission of ultrasound through the window cover to the tissue mimicking material. However, the relatively high rate of transmission of water vapor through such plastic films would permit unacceptable desiccation of the water based tissue mimicking material within the container in an unduly short period of time, typically within a year or two or sometimes less. Consequently, many phantoms were provided with layers of oil based gels over the water based gels, with the oil based gels in contact with the window covers.

In the present invention a layer of oil based gel is neither needed nor desired (although it still could be used but without significant purpose) by utilizing a cover in accordance with the invention which essentially blocks transmission of water vapor therethrough as well as blocking the transmission of air constituent molecules (e.g., oxygen, nitrogen, etc.) and organic molecules such as hydroxy typically found in the tissue mimicking material (e.g., n-propanol, ethylene glycol or glycerol). Moreover, the window cover of the present invention is tough and more puncture resistant than typical conventional flexible plastic scanning window covers. A particular advantage of the window cover of the present invention is its utilization in covering the side window 26, permitting the water based gels to be in direct contact with the window cover 26 without significant transmission of water vapor or air molecules therethrough, and with adequate structural strength to fully contain the pressure imposed by the tissue mimicking material 28 on the window cover.

In accordance with the invention, the top scanning window cover 24 and the side scanning window cover 26 are comprised of a multi-layer film that is formed of at least a layer of metal on a layer of plastic and may comprise a metal foil layer between layers of plastic. The metal layer and plastic layer(s) are selected to be sufficiently strong and thick to provide structural integrity, but also to transmit ultrasound pulses from an ultrasound transducer therethrough without substantial attenuation or echoes. The metal layer in accordance with the invention provides blockage of vapor and air molecule transmission but is found not to significantly affect the transmission of the ultrasound pulses at the thicknesses required to block vapor and air transmission, while retaining the desired flexibility for the multi-layer film. As used herein, a "plastic" layer is a layer of any material that is plastic like, including natural and synthetic rubbers, and other materials that can serve to carry and protect the metal layer.

Figure 5:
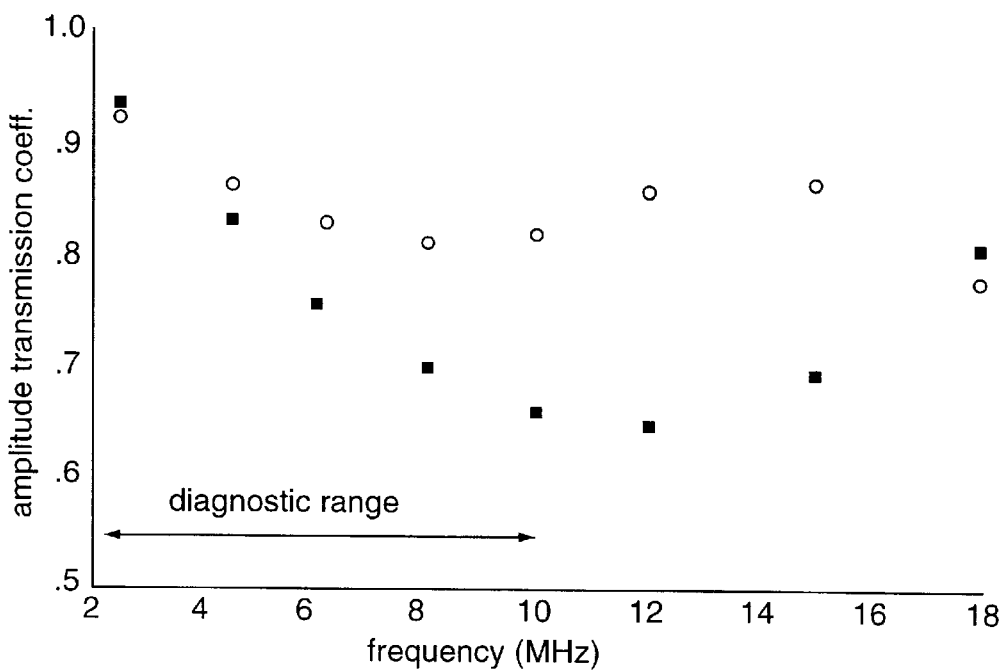
FIG. 5 are plots showing amplitude transmission coefficients as a function of frequency for a preferred material for forming a cover of the ultrasound phantom in accordance with the invention and similar amplitude transmission coefficients for a conventional phantom window cover formed of saran plastic.

A preferred multi-layer film in accordance with the invention comprises a 100 micrometer total thickness multi-layer structure comprising a 0.00035 inch (8.89 micrometer) thick layer of aluminum foil between layers of plastic; a layer of low density polyethylene (⅔ mil/16.93 $\mu$m) on one side, and on the other side a layer of ScotchPak® heat sealable film from Minnesota Mining and Manufacturing Company (63 $\mu$m thick), with an additional layer of PET polyester (polyethylene terepthalate) (12.192 $\mu$m thick), preferably with white ink on the PET, adhered to the layer of low density polyethylene. This multi-layer film material is available commercially from American Packaging Company, Rochester, New York. Such material has a moisture vapor transmission rate less than 0.01 grams at 100° F. and 90% relative humidity, and an oxygen transfer rate less than 0.01 cubic centimeters at 72° F. and 50% relative humidity, per 100 square inch area. FIG. 5 compares the measured amplitude transmission coefficient data for this plastic coated aluminum film with 50 micron thick saran (Saran Wrap®), both as a function of ultrasound frequency, which illustrates the acceptable amplitude transmission characteristics of the preferred material over the range of ultrasound frequencies utilized in medical diagnostic equipment. The data were taken in each case utilizing transmission from water through film to water at 22° C.

A multi-layer film comprising a layer of metal foil between layers of plastic is generally preferred because the plastic layers protect the metal from physical abrasion, oxidation and corrosion. An appropriate multi-layer film comprising a metal layer adhered to a plastic layer may be utilized. The metal layer preferably is not susceptible to corrosion when in contact with the tissue mimicking material. Such multi-layer films can include, for example, a layer of silver covered by a layer of inconel metal (a nickel/chromium alloy) both sputtered into a polyester film of 25 to 75 $\mu$m thickness (e.g., from Innovative Specialty Films, Inc.). The inconel metal is resistant to corrosion. The metal surface may be directly adhered (e.g., with epoxy) to the margins of the container walls defining the window(s). Multi-layer films incorporating other plastic materials may also be utilized. An example is a multi-layer film comprised of a layer of aluminum foil between layers of polyester, which is well suited to be adhered with a water resistant glue.

It is understood that the container 11 may be provided with additional side scanning window openings in the other side walls 15, 17 and 18, each covered by the plastic coated metal foil window cover in accordance with the invention, allowing the characteristics of the tissue mimicking material to be tested with an ultrasonic transducer from additional orientations and positions. Furthermore, as indicated above, the geometry of the container is not limited to the rectangular geometry shown, and for some purposes, the phantom may be formed to have no rigid walls at all.

Figure 6:
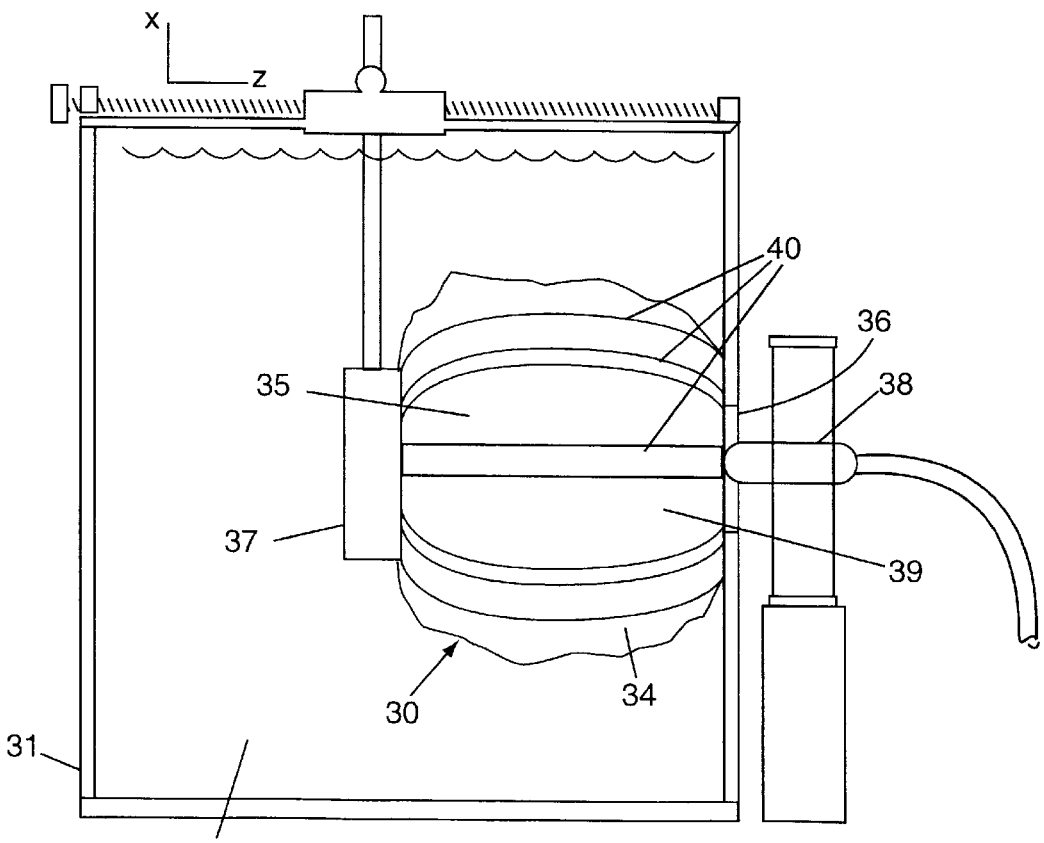
FIG. 6 is a simplified view of a phantom in accordance with the invention formed of flexible plastic immersed in a water bath within a container.

With reference to FIG. 6, a tissue mimicking phantom 30 in accordance with the invention is shown mounted within an enclosure 31 for holding a liquid (typically water) bath 32. The ultrasound phantom 30 comprises a flexible sack container 34 which surrounds and encloses a tissue mimicking material 35 within it, which may be solid or liquid. The structure of FIG. 6 is particularly useful with a water based liquid tissue mimicking material within the sack 34 since it allows coupling of ultrasound through the liquid material to a hydrophone 37, transmitted from an ultrasound transducer 38 through an opening 36 in a wall of the container 31 to the phantom 30. If desired, the hydrophone 37 may be mounted on a commercial x-y-z translator for positioning of the hydrophone. The flexible sack 34 is formed of a plastic coated metal foil material 39, particularly the preferred multi-layer film material as described above, which may be heat sealed utilizing the heat sealable Scotch-Pak® layer to provide the enclosed sack 34. Flexible plastic reinforcing strips 40 (e.g., 0.7 mm thick flexible polycarbonate strips attached to the walls of the enclosure 31) within the sack 34 may be used to provide structural support for the container sack 34. Because the multi-layer film 39 forming the walls of the container 34 is essentially impervious to transmission of water therethrough, the phantom 30 may be submerged in the water bath without transmission of water through the multi-layer film material 39 which, if it occurred, would change the characteristics of the tissue mimicking material within the container. The phantom 30 may utilize a liquid tissue mimicking material, an example of which is described in the aforesaid U.S. Pat. No. 5,625, 137. In the phantom testing system of FIG. 6, the opening 36 into the enclosure 31 for the bath may be closed with a multi-layer film of the same type as utilized for forming the walls of the phantom 30, or portions of the sack 34 may be sealed to the areas of the inner wall of the container 31 around the opening 36 to close off the opening.

The flexible walled phantom 30 may also be utilized as an insert into a rigid phantom enclosure, e.g., within the container 11 of FIGS. 1–4, eliminating the need for a top window cover 24 and a side window cover 26. Further, the phantom may be formed in accordance with the invention utilizing the multi-layer film sealed to the interior of a rigid container, such as the container 11, to further block transmission of vapors through the walls of the container and to prevent migration of compounds from the walls of the container into the tissue mimicking material or vice versa over time.

A further example of an ultrasound phantom 50 in accordance with the invention is illustrated in a top view in FIG. 7 and a cross-sectional view in FIG. 8. The phantom has a rigid container 51 formed of a bottom wall 52 and side walls 53, e.g., of acrylic or ABS plastic, which are joined together as by gluing or by being integrally formed together. A cover 56 of a multi-layer film of plastic coated metal material as described above closes the top of the container and seals tissue mimicking material 57 within the container. The cover 56 is secured at its edges to a frame 58 formed of material to which the multi-layer film can be sealed by gluing or heat sealing, etc. The frame 58 is then attached to the top edges of the side walls 53, e.g., by glue or screws, etc. In this way, the cover 56 can be oriented with a plastic layer facing the tissue mimicking material of the type (e.g., polyethylene) that could not readily be glued to the material of which the walls 53 are formed (e.g., acrylic or ABS plastic). If desired, one or more covered windows may be provided in the side walls 53 as discussed above.

In addition, panels 60 of multi-layer film of the type described above may be engaged to the inward sides of the bottom wall 52 and the side walls 53 to provide a barrier to moisture and gas transport through the bottom wall and side walls. The panels 60 may be separately attached to the walls or the panels may be joined together and form a bag for holding the tissue mimicking material that can be inserted into the rigid container.

FIGS. 9–12 illustrate steps in the assembly of the frame 58 with the window cover 56 glued thereto. The frame 58 is preferably formed of a thin sheet of material, such as acrylic or ABS plastic, having the shape of the outer walls of the container to which the frame is to be adhered. As illustrated in FIG. 9, the first step is to adhere the multi-layer film to the frame by utilizing an initial sheet 64 of the multi-layer film which is substantially larger than the frame 58. As illustrated in FIG. 10, the margins of the sheet 64 are then cutaway at razorblade cuts 67 and any remaining multi-layer film beyond the cuts may be scraped away to leave a 3 mm or 4 mm outer edge of the frame which is uncovered. A masking procedure using, e.g., a very thin polyethylene layer with a rectangular opening, may be used to separate the plastic from the frame. An alternative process is illustrated in the side view of FIG. 11 in which, for example, the sheet 64 may be supported on a base of, e.g., plate glass 68 with a support panel 69 of plate glass adhered thereto, the panel 69 having the rectangular dimension preferred for the multi-layer film after it is adhered to the frame. For example, the polyester side of the preferred multi-layer film described above may be glued to an acrylic or ABS frame 58 with super glue. As illustrated in FIG. 11, the base plate 69 is not as wide as the frame 58 and a 3 mm or 4 mm wide strip outside the base plate exists where the film sheet 64 is not glued to the frame.

Where the glass plate 68 and 69 of FIG. 11 are utilized, the multi-layer film 64 is stretched over the glass plate base 69 and is taped to the larger glass plate 68. A layer of, e.g., super glue may then be applied to the inner edge of the frame 58 and the frame lowered onto the projecting section of the multi-layer film 64. After the super glue has dried, the undesired portions of the sheet 64 may then be cut away to leave the bare acrylic or ABS edge of the frame for gluing to the container.

After the unwanted parts of the sheet 64 have been cut away, the completed frame assembly as is shown in FIG. 12 in which the multi-layer film cover 56 is adhered to the frame 58 along inner margins 70 and leaving an outer margin 71 along the outer edges of the frame which is not covered by the multi-layer film. The area 71 may then have glue applied thereto to glue the frame to the margins of the container. The frame may be glued to the container with, e.g., epoxy or other adhesives. For example, where the frame 58 and the container 51 are formed of acrylic plastic, an "acrylic glue" may be used which consists of methylene chloride made viscous by dissolving acrylic shavings in it.

It is understood that the invention is not confined to the particular embodiments set forth herein as illustrative, but embraces all such modified forms thereof as come within the scope of the following claims.

What is claimed is:

1. An ultrasound phantom for use with an ultrasound scanner, comprising:
   (a) a container having a bottom and walls, margins of the walls defining a window;
   (b) an ultrasound-transmitting window cover sealed to the margins defining the window to close the window, the window cover comprising a multi-layer film formed of at least a layer of metal adhered to a layer of plastic; and
   (c) a phantom body contained within the container comprising a water based tissue mimicking material.

2. The ultrasound phantom of claim 1 wherein the window is a top scanning window, and wherein a wall of the container has an opening formed therein defining a side scanning window opening and including a side window cover sealed to the wall to cover the side scanning window opening, the side window cover comprising a multi-layer film formed of at least a layer of metal foil between layers of plastic.

3. The ultrasound phantom of claim 1 wherein the material of the phantom body is in direct contact with the window cover.

4. The phantom of claim 1 wherein the multi-layer film comprises a layer of metal foil between layers of plastic.

5. The ultrasound phantom of claim 4 wherein the layer of metal foil in the multi-layer film is aluminum foil.

6. The phantom of claim 4 wherein at least one of the plastic layers that the metal foil is between is formed of polyethylene.

7. The ultrasound phantom of claim 6 wherein the multi-layer film further includes a layer of polyester plastic over at least one of the layers that the metal foil is between.

8. The ultrasound phantom of claim 4 wherein at least one of the plastic layers that the metal foil is between is formed of polyester.

9. The ultrasound phantom of claim 4 wherein the plastic layers that the metal foil is between are formed of polyester.

10. The ultrasound phantom of claim 1 wherein the window cover is sealed to the margins of the walls with adhesive.

11. The ultrasound phantom of claim 1 wherein the tissue mimicking material is a water based gel.

12. The ultrasound phantom of claim 1 wherein the tissue mimicking material is liquid.

13. The ultrasound phantom of claim 1 wherein the multi-layer film comprises metal foil between layers of plastic and the metal foil in the multi-layer film is aluminum and has a thickness less than about 10 $\mu$m.

14. The ultrasound phantom of claim 1 further including panels comprising a multi-layer film formed of at least a layer of metal foil between layers of plastic that are engaged to inward sides of the bottom wall and side walls.

15. An ultrasound phantom for use with an ultrasound scanner, comprising:
   (a) a container having a bottom and walls, and wherein a wall of the container has an opening formed therein defining a side scanning window opening;

(b) an ultrasound-transmitting window cover sealed to the wall having an opening to cover the side scanning window opening, the side window cover comprising a multi-layer film formed of at least a layer of metal adhered to a layer of plastic; and (c) a phantom body contained within the container comprising a water based tissue mimicking material.

16. The ultrasound phantom of claim 15 wherein the material of the phantom body is in direct contact with the window cover.

17. The ultrasound phantom of claim 15 wherein the multi-layer film comprises metal foil between layers of plastic.

18. The ultrasound phantom of claim 17 wherein the layer of metal foil in the multi-layer film is aluminum and has a thickness less than about 10 $\mu$m.

19. The phantom of claim 17 wherein at least one of the plastic layers that the metal foil is between is formed of polyethylene.

20. The ultrasound phantom of claim 19 wherein the multi-layer film further includes a layer of polyester plastic over at least one of the layers that the metal foil is between.

21. The ultrasound phantom of claim 17 wherein at least one of the layers that the metal foil is between is formed of polyester.

22. The ultrasound phantom of claim 17 wherein the plastic layers that the metal foil is between are formed of polyester.

23. The ultrasound phantom of claim 15 wherein the window cover is sealed to the wall with adhesive.

24. The ultrasound phantom of claim 15 wherein the tissue mimicking material is a water based gel.

25. The ultrasound phantom of claim 15 wherein the tissue mimicking material is liquid.

26. The ultrasound phantom of claim 15 further including panels comprising a multi-layer film formed of at least a layer of metal foil between layers of plastic that are engaged to inward sides of the bottom wall and side walls.

27. An ultrasound phantom for use with an ultrasound scanner, comprising:

(a) a container having walls comprising a multi-layer film formed of at least a layer of metal between layers of plastic; and (b) a phantom body contained within the container comprising a water based tissue mimicking material.

28. The ultrasound phantom of claim 27 further including an enclosure for a water bath, the container of the ultrasound phantom mounted within the enclosure for the water bath and against an opening in a side wall of the enclosure that defines a window to allow access by an ultrasound transducer to the ultrasound phantom within the water bath.

29. The ultrasound phantom of claim 28 further comprising a cover for the opening in the enclosure for the water bath sealed to the wall of the enclosure, the cover comprising a multi-layer film formed of at least a layer of metal foil between layers of plastic.

30. The ultrasound phantom of claim 28 wherein the walls of the container are sealed to portions of the wall of the enclosure surrounding the opening in the enclosure to seal off the opening.

31. The ultrasound phantom of claim 27 wherein the layer of metal is aluminum foil.

32. The ultrasound phantom of claim 31 wherein at least one of the plastic layers that the metal foil is between is formed of polyethylene.

33. The ultrasound phantom of claim 27 further including a layer of polyester plastic over at least one of the layers that the metal foil is between.

34. The ultrasound phantom of claim 27 wherein the tissue mimicking material is liquid.

35. The ultrasound phantom of claim 27 wherein the metal in the multi-layer film is aluminum and has a thickness less than about 10 $\mu$m.

* * * * *